United States Patent
Fan et al.

(10) Patent No.: US 10,184,902 B2
(45) Date of Patent: Jan. 22, 2019

(54) SUBSTRATE SURFACE INFORMATION DETECTION DEVICE AND SUBSTRATE SURFACE INFORMATION DETECTION METHOD

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Yuguang Fan, Beijing (CN); Jingpeng Li, Beijing (CN); Jian Li, Beijing (CN); Shichao Wang, Beijing (CN); Limin Tian, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/542,179

(22) PCT Filed: Jun. 3, 2016

(86) PCT No.: PCT/CN2016/084761
§ 371 (c)(1),
(2) Date: Jul. 7, 2017

(87) PCT Pub. No.: WO2017/140069
PCT Pub. Date: Aug. 24, 2017

(65) Prior Publication Data
US 2018/0067059 A1    Mar. 8, 2018

(30) Foreign Application Priority Data
Feb. 16, 2016 (CN) .......................... 2016 1 0087753

(51) Int. Cl.
*G01J 3/44*  (2006.01)
*G01N 21/95*  (2006.01)
(Continued)

(52) U.S. Cl.
CPC ....... *G01N 21/9501* (2013.01); *G01N 21/894* (2013.01); *G01P 13/0006* (2013.01);
(Continued)

(58) Field of Classification Search
CPC .......... G01N 2021/945; G01N 21/894; G01N 21/9501; G01N 2021/9513; G01P 13/0006; G02F 1/1309; G02F 1/13
(Continued)

(56) References Cited

U.S. PATENT DOCUMENTS 7,248,346 B2 * 7/2007 Ho ................... G02F 1/133711
356/36
2005/0158653 A1 * 7/2005 Hatakeyama ........ G01N 23/225
430/270.1

FOREIGN PATENT DOCUMENTS

CN    1690698 A    11/2005
CN    101089680 A    12/2007
(Continued)

OTHER PUBLICATIONS

Image analysis of hydrophobicity of polymer insulators using PVM Author(s): Tokoro T.(1); Omoto Y.(1); Kosaki M.(1), 2001 Annual Report conference on electrical insulation and dielectric phenomena, p. 581-584.*
(Continued)

*Primary Examiner* — Sunghee Y Gray
(74) *Attorney, Agent, or Firm* — Ladas & Parry LLP

(57) ABSTRACT

A substrate surface information detection device and a substrate surface information detection method are disclosed. The device includes a spray source and an image
(Continued)

sensor, wherein the spray source is configured to uniformly spray droplets onto a surface of a substrate-under-test or form a liquid flow on the surface of the substrate-under-test, and the image sensor is configured to record image information of the droplets or the liquid flow. According to the substrate surface information detection device and substrate surface information detection method, defects on the surface of the substrate before the PI coating can be prevented and avoided, the production time can be shortened, and the production efficiency can be promoted and the product yield can be improved.

2 Claims, 6 Drawing Sheets

(51) Int. Cl.
*G01N 21/894* (2006.01)
*G01P 13/00* (2006.01)
*G02F 1/13* (2006.01)
*G01N 21/94* (2006.01)

(52) U.S. Cl.
CPC ..... *G02F 1/1309* (2013.01); *G01N 2021/945* (2013.01); *G01N 2021/9513* (2013.01)

(58) Field of Classification Search
USPC .......................................................... 356/600
See application file for complete search history.

(56) References Cited

FOREIGN PATENT DOCUMENTS

| CN | 101324713 A | 12/2008 |
| CN | 103399021 A | 11/2013 |
| CN | 103412421 A | 11/2013 |
| CN | 104122229 A | 10/2014 |
| CN | 104317077 A | 1/2015 |
| CN | 104568989 A | 4/2015 |
| JP | 2002-057761 A | 2/2002 |
| KR | 20080026995 A | 3/2008 |

OTHER PUBLICATIONS

The International Search Report and Written Opinion dated Nov. 15, 2016; PCT/CN2016/084761.
The First Chinese Office Action dated Jun. 4, 2018; Appln. No. 20160087753.X.

* cited by examiner

SUBSTRATE SURFACE INFORMATION DETECTION DEVICE AND SUBSTRATE SURFACE INFORMATION DETECTION METHOD

TECHNICAL FIELD

Embodiments of the present disclosure relate to a device and a method for substrate surface information detection.

BACKGROUND

In the preparation of thin film transistor liquid crystal display (TFT-LCD), polyimide (PI) coating process is a very important part. The PI coating is typically carried out by use of polyamic acid or polyimide solution in a manner of passing through a photosensitive resin plate (alignment film printing plate) or spraying. When the PI coating is finished, after leveling, pre-curing and curing, orientation is carried out through friction orientating or light curing orientating, and then by dropping the liquid crystal, cell assembling and cutting, a conventional TFT-LCD liquid crystal cell is formed. During the course of PI coating, there might be defects such as pinhole-like defects caused by unevenness of the substrate surface. Such pinhole-like defects in the TFT-LCD are often embodied as white or black spots.

At present, the aforementioned problem is mainly solved by making repairs after the defects appear.

SUMMARY

At least one embodiment of the present disclosure provides a substrate surface information detection device, comprising a spray source and an image sensor, wherein the spray source is configured to uniformly spray droplets onto a surface of a substrate-under-test or form a liquid flow on the surface of the substrate-under-test, and the image sensor is configured to record image information of the droplets or the liquid flow. If the substrate-under-test has an unevenness in a partial region or has a contamination by metal residue or fallen foreign matter and by oil during manufacturing process, the partial region will have different surface tension due to the above situation, so that the liquid will have different state on the surface of the substrate-under-test. The spray source is configured to uniformly spray the droplets onto the substrate-under-test or to form a liquid flow on the substrate-under-test, and the liquid is adhered to the surface of the substrate-under-test. The image sensor 12 is configured to record image information that the liquid exhibits different states due to the surface condition of the substrate-under-test, and the surface condition of the substrate-under-test is obtained by analyzing the image information.

At least one embodiment of the present disclosure provides a substrate surface information detection method, comprising:

spraying droplets uniformly onto a substrate-under-test which is horizontally arranged, or forming a liquid flow on a surface of the substrate-under-test;

obtaining image information of the surface of the substrate-under-test, obtaining surface information of the substrate-under-test based on the image information, the surface information including comprising at least one of flatness, cleanliness and hydrophilicity/hydrophobicity in at least a partial region of the surface of the substrate-under-test.

By spraying droplets uniformly onto a substrate-under-test or forming a liquid flow on a surface of the substrate-under-test, attaching the liquid to the surface of the substrate-under-test, and recording the image information exhibiting different states due to the surface condition of the substrate-under-test, and determining the image information, at least one of flatness, cleanliness and hydrophilicity/hydrophobicity in the partial region of the surface of the substrate-under-test can be obtained. The surface information detection device and the surface information detection method according to embodiments of the present disclosure can prevent and avoid the defects on the surface of the substrate before the PI coating, and have a positive effect on shortening the production time and promoting the production efficiency and improving the product yield.

BRIEF DESCRIPTION OF THE DRAWINGS

In order to clearly illustrate the technical solutions of the embodiments of the disclosure, the drawings of the embodiments will be briefly described in the following; it is obvious that the drawings described below are only related to some embodiments of the disclosure and thus are not limitative of the disclosure.

Figure 1:
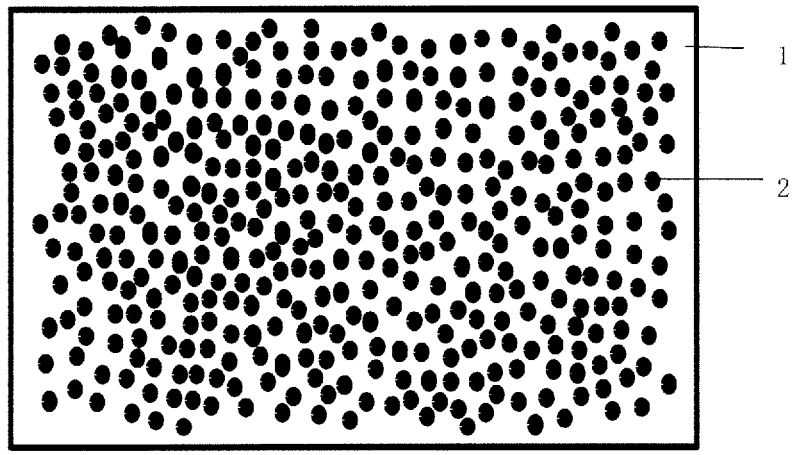
FIG. 1 is a schematic view of liquid image information formed by spraying droplets onto a substrate-under-test according to an embodiment of the present disclosure.

REFERENCE NUMERALS 1 substrate-under-test;
2 droplet;
3 droplet in a defective region of the surface of the substrate-under-test;
4 defective region of the surface of the substrate-under-test;
5 direction of liquid flow;

6 liquid flow;
7 liquid flow in a defective region of the surface of the substrate-under-test;
11 spray source;
12 image sensor;
13 image determining and processing unit.

DETAILED DESCRIPTION

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Figure 10:
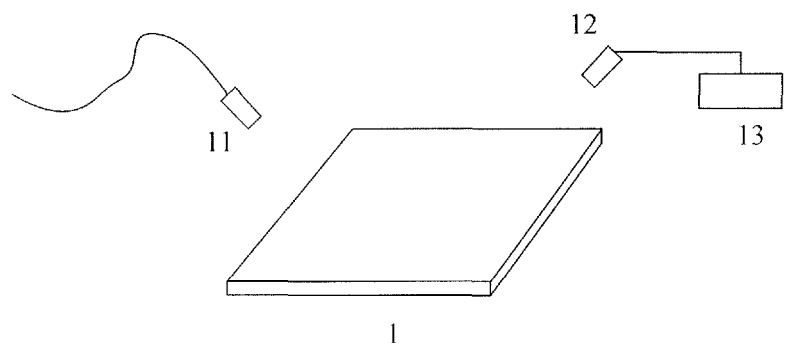
FIG. 10 is a system block diagram of a substrate surface information detection device according to an embodiment of the present disclosure.

At least one of the embodiments of the present disclosure provides a substrate surface information detection device, as illustrated in FIG. 10, comprising a spray source and an image sensor. The spray source 11 is configured to uniformly spray droplets 2 onto a substrate-under-test 1, and the image sensor 12 is configured to record liquid image information of a surface of the substrate-under-test 1. If the substrate-under-test 1 has an unevenness in a partial region or has a contamination by metal residue or fallen foreign matter and by oil during manufacturing process, the partial region will have different surface tension due to the above situation, so that the liquid will have different state on the surface of the substrate-under-test 1. The spray source 11 is configured to uniformly spray the droplets 2 onto the substrate-under-test 1 or to form a liquid flow 7 on the substrate-under-test 1, and the liquid is adhered to the surface of the substrate-under-test 1. The image sensor 12 is configured to record image information that the liquid exhibits different states due to the surface condition of the substrate-under-test 1, and the surface condition of the substrate-under-test 1 is obtained by analyzing the image information.

Figure 3:
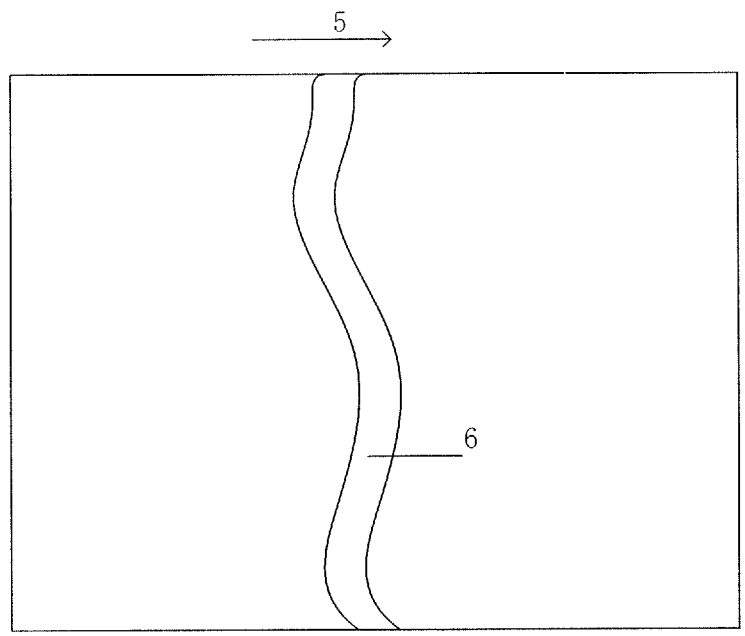
FIG. 3 is a schematic view of liquid image information formed by forming a liquid flow on a surface of a substrate-under-test according to an embodiment of the present disclosure.

If the surface condition of the substrate-under-test 1 is good, then when the spray source 11 uniformly sprays the droplets 2 onto the substrate-under-test 1, the image information as illustrated in FIG. 1 will be presented on the substrate-under-test 1, in which the droplets 2 are uniformly distributed on the substrate-under-test 1; and when the spray source 11 forms a liquid flow 6 on the substrate-under-test 1 along a direction 5, the liquid image information as illustrated in FIG. 3 will be presented on the substrate-under-test 1, in which the liquid flow 6 has a uniform width.

Figure 2:
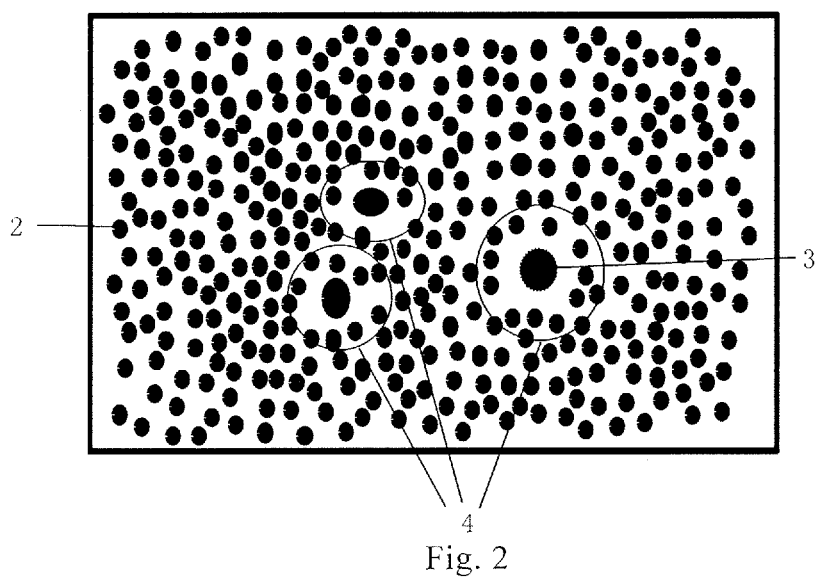
FIG. 2 is a schematic view of liquid image information formed by spraying droplets onto a surface of a substrate-under-test where an abnormal region exists according to an embodiment of the present disclosure.
Figure 4:
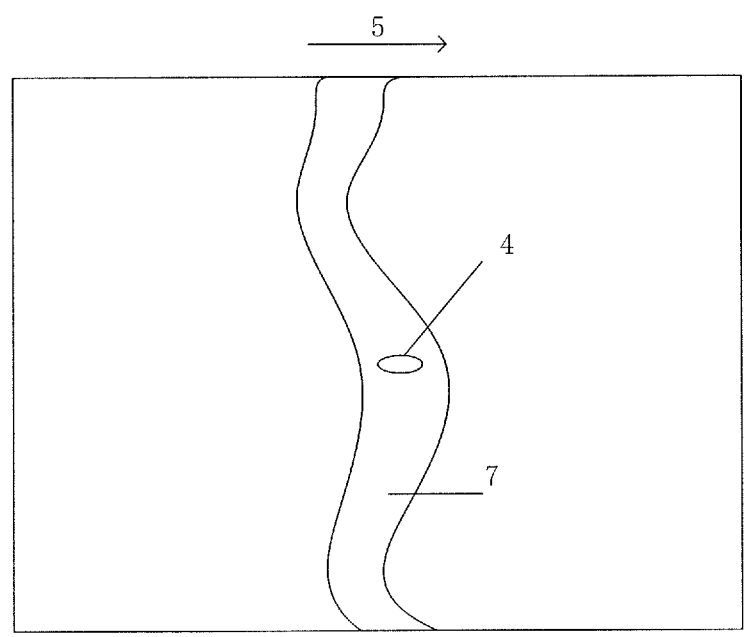
FIG. 4 is a schematic view of liquid image information formed by forming a liquid flow on a surface of a substrate-under-test where an abnormal region exists according to an embodiment of the present disclosure.

If the surface condition of the substrate-under-test 1 is not good, for example, a partial region has an unevenness surface or there is a contamination by metal residue or fallen foreign matter and by oil during the manufacturing process, then when the spray source 11 uniformly sprays the droplets 2 onto the substrate-under-test 1, the liquid image information as illustrated in FIG. 2 will be presented, wherein in the uneven or contaminated position, such as in the position 4, due to an abnormal surface tension, adjacent droplets are brought together to form a relatively large droplet such as a droplet 3; and when the spray source 11 forms a liquid flow 7 on the substrate-under-test 1 along a direction 5, due to the unevenness and contamination in the partial region of the substrate-under-test 1, for example in the position 4, the image information as illustrated in FIG. 4 will be presented, wherein the liquid flow 7 is disturbed by the uneven region or the contamination in the position 4, and its width changes in the position 4.

In another embodiment of the present disclosure, the surface information detection device of the substrate-under-test 1 further comprises an image determining and processing unit. The image determining and processing unit 13 is configured to receive image information from the image sensor 12 and determine the surface information of the substrate-under-test 1 based on the image information, the surface information including at least one of evenness, cleanliness and hydrophilicity/hydrophobicity in at least a partial region of the surface of the substrate-under-test 1. Since at least one of flatness, cleanliness and hydrophilicity/hydrophobicity in the partial region of the substrate-under-test 1 is varied, the aforementioned state information of the surface of substrate-under-test 1 can be obtained by determining the liquid image information recorded by the image sensor 12.

The image information illustrated in FIG. 1 and FIG. 3 indicates that the entire surface of the substrate-under-test 1 is consistent in evenness, cleanliness and hydrophilicity/hydrophobicity. The image information illustrated in FIG. 2 and FIG. 4 indicates that various regions of the surface of the substrate-under-test 1 are different in at least one of flatness, cleanliness and hydrophilicity/hydrophobicity.

It is to be noted that human eye can also be used as the image determining and processing unit and the aforementioned state information of the surface of substrate-under-test 1 can be obtained by determining the liquid image information recorded by the image sensor 12 likewise.

In another embodiment of the present disclosure, the image determining and processing unit 13 is further configured to determine the position of the region in the surface of the substrate-under-test 1 whose flatness, and/or cleanliness and/or hydrophilicity/hydrophobicity is/are beyond the preset range based on the image information. In implementation, the preset range of the flatness, or cleanliness or hydrophilicity/hydrophobicity of the substrate-under-test 1 can be set as required. When an abnormal region beyond the preset range is found in the image information, the image determining and processing unit 13 can determine the position of the abnormal region.

In one embodiment of the present disclosure, the droplet 2 has a diameter in the range of 0.1 m to 1000 μm. In this embodiment, the substrate-under-test 1 is a liquid crystal display substrate. According to a size of sub-pixel cells in the liquid crystal display substrate, the droplet 2 having a diameter within the above range which is sprayed from the spray source 11 can detect the surface information of a region of the liquid crystal display substrate corresponding to each sub-pixel cell.

In another embodiment of the present disclosure, the droplet 2 has a diameter in the range of 1 μm to 30 μm. The droplet 2 having a diameter within this range can more precisely indicate the surface region information of a smaller unit in the substrate 1.

In one embodiment of the present disclosure, a flow rate of the liquid flow 6 ranges from 0.1 mm/s to 100 mm/s. The liquid flow 6 having a flow rate within this range can clearly determine the information of the surface region of a distance unit of the substrate-under-test 1.

In one embodiment of the present disclosure, the flow rate of the liquid flow 6 ranges from 1 mm/s to 10 mm/s.

In one embodiment of the present disclosure, the droplet 2 or the liquid flow 6 is deionized water. By use of deionized water, the surface information of the substrate-under-test 1 can be detected without contaminating the surface of the substrate-under-test 1.

In one embodiment of the present disclosure, the substrate-under-test 1 is placed below the spray source providing the liquid flow 7 at an angle of 3° to 10° inclined with respect to a horizontal direction. Compared with the substrate-under-test 1 placed horizontally, the substrate-under-test 1 tilted at an angle facilitates liquid flowing through the surface of the substrate-under-test 1, which makes the detection of the surface of the substrate-under-test 1 more convenient.

Figure 5:
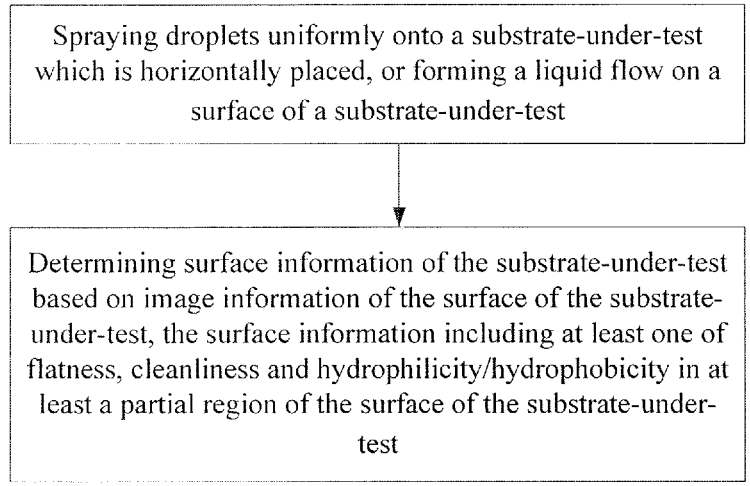
FIG. 5 is a flow chart of a substrate surface information detection method according to an embodiment of the present disclosure.

At least one embodiment of the present disclosure further provides a substrate surface information detection method, as illustrated in FIG. 5, comprising:

spraying droplets 2 uniformly onto a substrate-under-test 1 which is horizontally placed, or forming a liquid flow 6 on a surface of a substrate-under-test 1; and determining surface information of the substrate-under-test 1 based on image information of the surface of the substrate-under-test 1, the surface information including at least one of flatness, cleanliness and hydrophilicity/hydrophobicity in at least a partial region of the surface of the substrate-under-test 1.

By spraying droplets 2 or forming a liquid flow 6 on the substrate-under-test 1, the liquid is adhered to the surface of the substrate-under-test 1. By recording the image information exhibiting different states due to the surface condition of the substrate-under-test 1, and by determining the image information, at least one of flatness, cleanliness and hydrophilicity/hydrophobicity in the partial region of the surface of the substrate-under-test 1 can be obtained.

Figure 6:
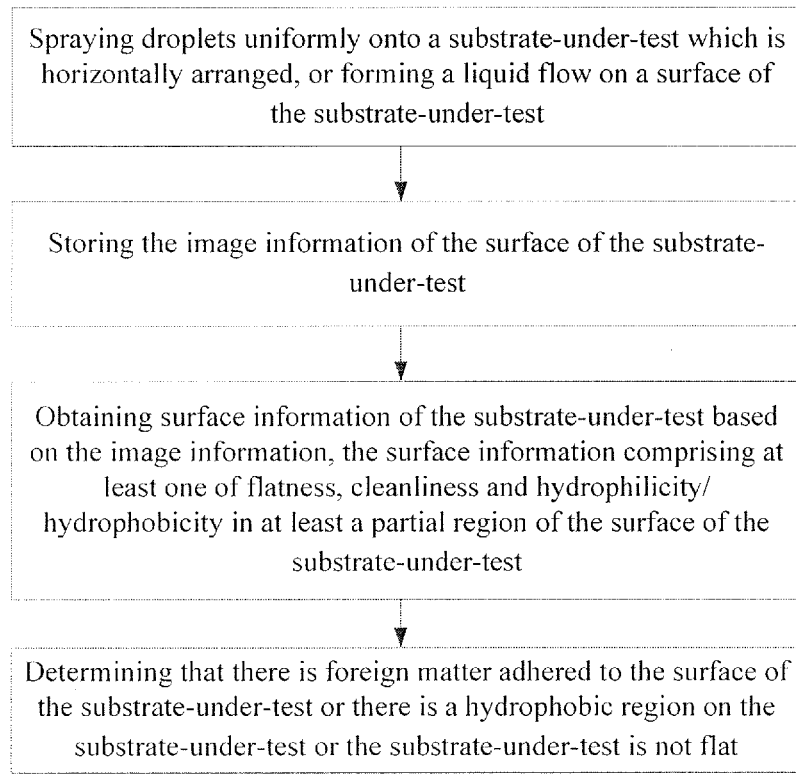
FIG. 6 is a flow chart of another substrate surface information detection method according to an embodiment of the present disclosure.

In one embodiment of the present disclosure, as illustrated in FIG. 6, before determining the surface information of the substrate-under-test based on the image information, the method further comprises storing the image information of the surface of the substrate-under-test. This facilitates the subsequent and more detailed analysis on the surface information of the substrate-under-test.

If the surface condition of the substrate-under-test 1 is good, then when the spray source 11 uniformly sprays the droplets 2 onto the substrate-under-test 1, the image information illustrated in FIG. 1 will be presented by way of example. The ratio of the size of the droplets to the size of the substrate-under-test in FIG. 1 does not reflect the actual proportions, but only for the purpose of illustration.

When the spray source 11 forms a liquid flow 6 on the substrate-under-test 1, the liquid flow 6 can partially or fully cover the substrate. By way of example, the image information illustrated in FIG. 3 may be presented.

If there is no foreign matter adhered to the surface of the substrate-under-test 1 or the surface of the substrate-under-test 1 has consistent hydrophilicity/hydrophobicity or all over the surface of the substrate-under-test 1 is even, the droplet size and/or the spacing between the adjacent droplets are/is relatively uniform, and the thus-formed droplets are illustrated in FIG. 1 by way of example. Otherwise, in case that the image information illustrated in FIG. 2 is presented, i.e., there is a relatively large droplet such as the droplet 3, it is indicated that there is foreign matter adhered to the surface of the substrate-under-test 1 or there are regions on the substrate-under-test 1 having different hydrophilicity/hydrophobicity or the substrate-under-test 1 is not even.

If there is no foreign matter adhered to the surface of the substrate-under-test 1 or the surface of the substrate-under-test 1 has consistent hydrophilicity/hydrophobicity or all over the surface of the substrate-under-test 1 is even, the surface of the liquid film formed by the liquid flow is relatively flat, which is illustrated in FIG. 3 by way of example. Otherwise, in case that the image information illustrated in FIG. 4 is presented, i.e., the surface of the liquid film formed by the liquid flow 7 is not flat, it is indicated that there is foreign matter adhered to the surface of the substrate-under-test 1 or there are regions on the substrate having different hydrophilicity/hydrophobicity or the substrate is not even.

In one embodiment of the present disclosure, in the process of forming the liquid flow 6 on the substrate-under-test 1, the substrate-under-test 1 is arranged to be inclined at an angle of 3° to 10° with respect to the horizontal direction. Compared with the substrate-under-test 1 arranged horizontally, the substrate-under-test 1 tilted at an angle facilitates liquid flowing through the surface of the substrate 1, which facilitates the detection of the surface of the substrate-under-test 1.

In one embodiment of the present disclosure, in the process of uniformly spraying the droplet 2 onto the substrate-under-test 1 arranged horizontally, the droplet 2 has a diameter in the range of 0.1 μm to 1000 μm. According to the size of the sub-pixel cells in the substrate-under-test 1, the sprayed droplet 2 having a diameter within the above range can indicate the surface information of a region of the substrate-under-test 1 corresponding to each sub-pixel cell.

In one embodiment of the present disclosure, the droplet 2 has a diameter in the range of 1 μm to 30 μm. The droplet 2 having a diameter within this range can more precisely detect the surface information of a region of a smaller unit in the substrate-under-test 1.

In one embodiment of the present disclosure, in the processing of providing a liquid flow from the spray source 11, the flow rate of the liquid flow ranges from 0.1 mm/s to 100 mm/s. The liquid flow having a flow rate within this range can clearly determine the surface information of a region of the substrate-under-test 1 corresponding to a unit distance.

In one embodiment of the present disclosure, the flow rate of the liquid flow 6 ranges from 1 mm/s to 10 mm/s.

Figure 7:
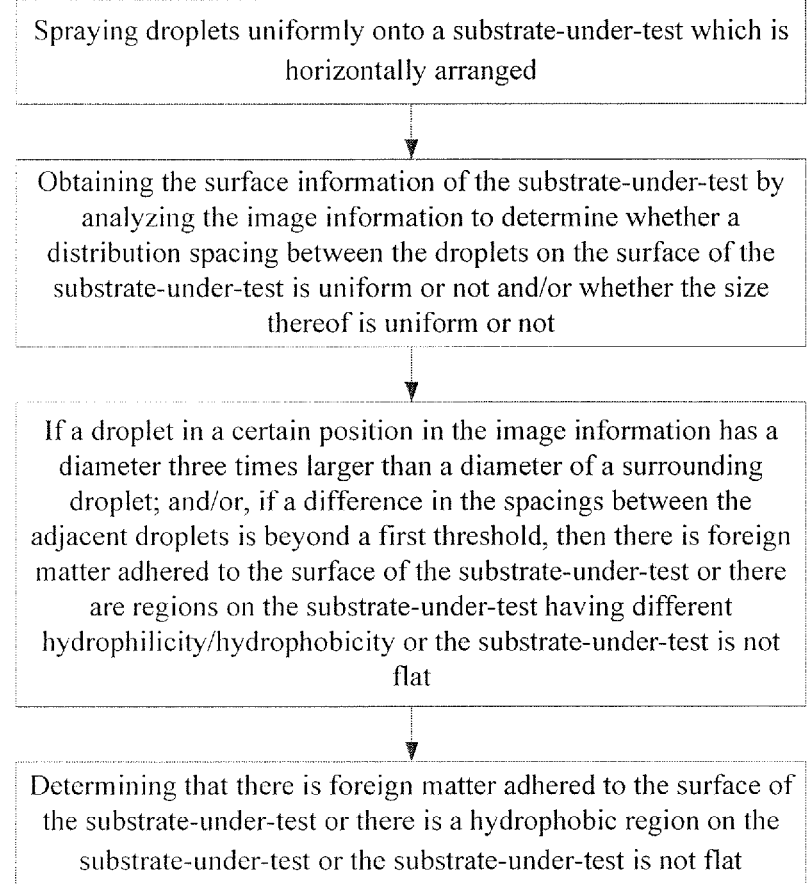
FIG. 7 is a flow chart of still another substrate surface information detection method according to an embodiment of the present disclosure.
Figure 8:
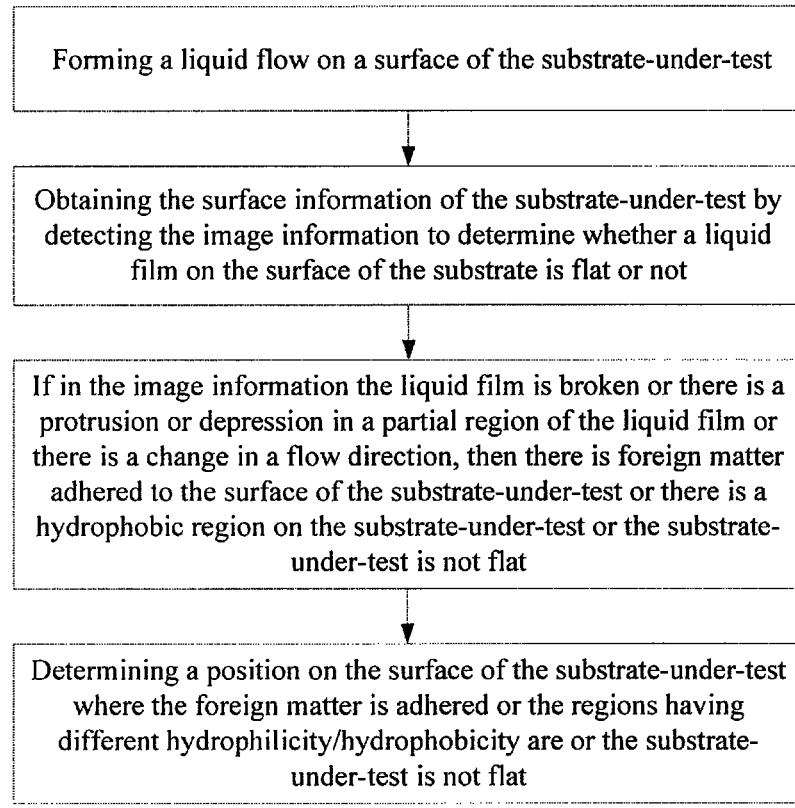
FIG. 8 is a flow chart of yet another substrate surface information detection method according to an embodiment of the present disclosure.

In one embodiment of the present disclosure, as illustrated in FIG. 7 and FIG. 8, determining the surface information of the substrate-under-test 1 based on the image information comprises obtaining the surface information of the substrate-under-test 1 by analyzing the image information to determine whether spacing between adjacent droplets on the surface of the substrate-under-test 1 is uniform or not and/or whether the droplet size is uniform or not; or obtaining the surface information of the substrate-under-test 1 by detecting the image information to determine whether the liquid film on the surface of the substrate-under-test 1 is flat or not.

By way of example, as illustrated in FIG. 2, the difference in the spacing between the adjacent droplets on the surface of the substrate-under-test 1 in the image information is too great, specifically the droplets in the regions 4 have a significantly larger distance between two adjacent droplets than the droplets in other regions; and/or, for example the droplet 2 and the droplet 3 vary greatly in size.

Alternatively, by way of example, as illustrated in FIG. 4, the liquid flow 7 on the surface of the substrate-under-test 1 becomes uneven or broken in the region 4.

In one embodiment of the present disclosure, as illustrated in FIG. 6 and FIG. 7, obtaining the surface information of the substrate-under-test 1 by analyzing the image information to determine whether the spacing between the adjacent droplets on the surface of the substrate-under-test 1 is uniform or not and/or whether the droplet size is uniform or not comprises:

determine in the image information whether the droplet in a certain position on the surface of the substrate-under-test 1 has a diameter three times larger than the diameter of a droplet around it; and/or, whether the difference in the spacing between the adjacent droplets on the surface of the substrate-under-test 1 is beyond a first threshold, the surface information of the substrate-under-test obtained including that there is foreign matter adhered to the surface of the substrate-under-test or there are regions on the substrate having different hydrophilicity/hydrophobicity or the substrate is not flat.

By way of example, as illustrated in FIG. 2, when there is foreign matter adhered to the surface of the substrate-under-test 1 or there is a defective surface region 4 such as a hydrophilic region or a recess region on the substrate, the droplets are gathered in this region, and forms a state like the droplet 3 having a much larger diameter than the surrounding droplets; and/or the difference in the spacing between the adjacent droplets in the region 4 is significantly larger than the difference in the spacing between the adjacent droplets in other regions. It is to be noted that the first threshold can be set according to the requirement for the measurement precision. When the difference in the spacing between the adjacent droplets is larger than the first threshold, it can be determined that there is foreign matter adhered to the surface of the substrate-under-test 1 or there is a hydrophilic region or a recess region on the surface of the substrate-under-test 1.

In one embodiment of the present disclosure, obtaining the surface information of the substrate-under-test 1 by detecting the image information to determine whether the liquid film on the surface of the substrate-under-test 1 is even or not comprises:

If in the image information the liquid film on the surface of the substrate-under-test 1 is broken or there is a protrusion or depression in a partial region of the liquid film or there is a change in the flow direction, then it is determined that there is foreign matter adhered to the surface of the substrate-under-test 1 or there are regions on the substrate having different hydrophilicity/hydrophobicity or the substrate is not flat.

By way of example, as illustrated in FIG. 4, when there is foreign matter adhered to the surface of the substrate-under-test 1 or there is a defective surface region 4 such as a hydrophilic region or a recess region on the surface of the substrate-under-test 1, the liquid flow 7 will form a protrusion or depression in the defective surface region 4 of the substrate-under-test or there will be change in the flow direction, which might cause breaking.

As illustrated in FIG. 6, FIG. 7 and FIG. 8, the substrate surface information detection method provided by one embodiment of the present disclosure further comprises:

determining the position on the surface of the substrate-under-test where the foreign matter is adhered or the regions having different hydrophilicity/hydrophobicity are or the substrate has an unevenness. After determining the position of the defective region on the surface of the substrate-under-test, remedial and appropriate measures can be taken to prevent the defects from affecting subsequent processes.

Figure 9:
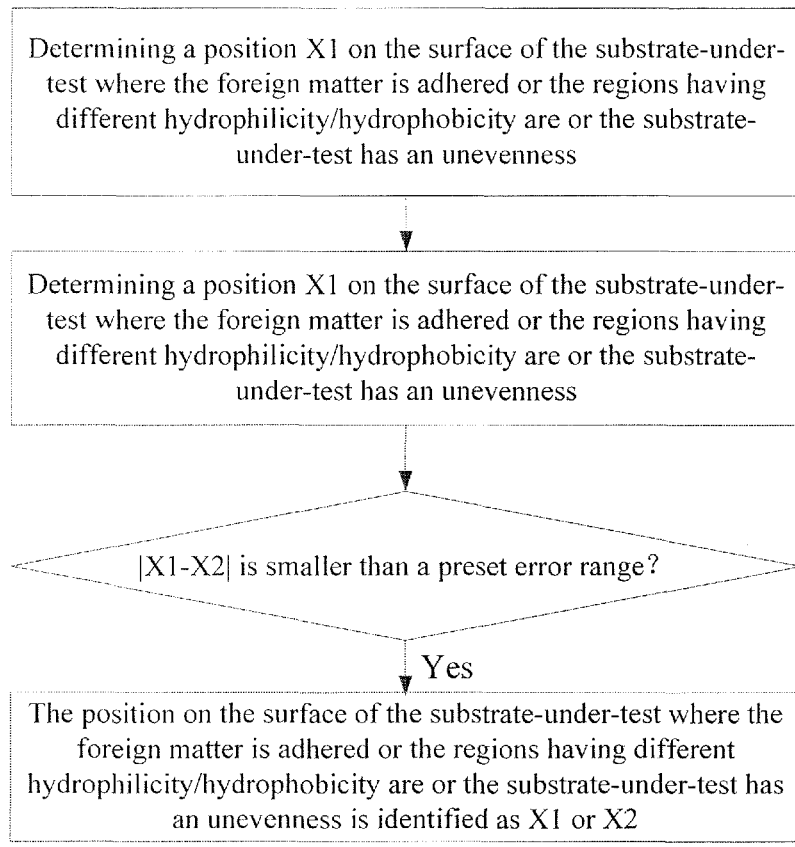
FIG. 9 is a flow chart of determining foreign matter attached to the substrate surface or a hydrophilic/hydrophobic characteristic region on the substrate or the position in the substrate having an unevenness in a substrate surface information detection method according to an embodiment of the present disclosure.

In one embodiment of the present disclosure, determining the position on the surface of the substrate-under-test where the foreign matter is adhered or the regions having different hydrophilicity/hydrophobicity are or the substrate has an unevenness is performed twice. If the difference of two determined positions is within the error range, then any one of the two determined positions is determined as the position on the surface of the substrate-under-test where the foreign matter is adhered or the regions having different hydrophilicity/hydrophobicity are or the substrate-under-test has an unevenness. As illustrated in FIG. 9, determining the position on the surface of the substrate-under-test where the foreign matter is adhered or the regions having different hydrophilicity/hydrophobicity are or the substrate-under-test has an unevenness comprises:

determining a position X1 on the surface of the substrate-under-test where the foreign matter is adhered or the regions having different hydrophilicity/hydrophobicity are or the substrate-under-test has an unevenness;

determining a position X2 on the surface of the substrate-under-test where the foreign matter is adhered or the regions having different hydrophilicity/hydrophobicity are or the substrate-under-test has an unevenness;

calculating the difference between the two positions X1 and X2, if the difference between the positions $|X1-X2|$ is smaller than a preset error range, wherein the interval value of the preset error range is selected, then the position on the surface of the substrate-under-test where the foreign matter is adhered or the regions having different hydrophilicity/hydrophobicity are or the substrate-under-test has an unevenness is identified as X1 or X2.

Thus, appropriate remedial measures can be taken against the defective regions in a more accurate and targeted manner.

It is to be noted that the number of times for performing determining the position on the surface of the substrate-under-test where the foreign matter is adhered or the regions having different hydrophilicity/hydrophobicity are or the substrate-under-test has an unevenness is not limited to two, if the number of times performing the method is N, wherein N is greater than 2, by way of example, the differences between every two of N determined positions are calculated, in case that more than half of the differences is within the error range, then the average of the N determined positions results can be determined as the position on the surface of the substrate-under-test where the foreign matter is adhered or the regions having different hydrophilicity/hydrophobicity are or the substrate-under-test has an unevenness.

The surface information detection method of the substrate-under-test according to the embodiments of the present disclosure can prevent and avoid the defects on the surface of the substrate before the PI coating, and have a positive effect on shortening the production time and improving the production efficiency and improving the product yield.

The foregoing are merely exemplary embodiments of the disclosure, but are not used to limit the protection scope of the disclosure. The protection scope of the disclosure shall be defined by the attached claims.

The present disclosure claims priority of Chinese Patent Application No. 201610087753.X filed on Feb. 16, 2016, the disclosure of which is hereby entirely incorporated by reference as a part of the present disclosure.

The invention claimed is:

1. A substrate surface information detection device, comprising a spray source and an image sensor, wherein the spray source is configured to form a liquid flow on the surface of the substrate-under-test, and the image sensor is configured to record image information of the liquid flow; and an image determining and processing unit, which is configured to receive the image information from the image sensor and obtain surface information of the substrate-under-test from the image information, the surface information including at least one of flatness, cleanliness and hydrophilicity/hydrophobicity in at least a partial region of the surface of the substrate-under-test, wherein the image determining and processing unit is configured to obtain the surface information of the substrate-under-test based on surface flatness of a liquid film formed by the liquid flow in the image information.

2. The substrate surface information detection device according to claim 1, wherein the image determining and processing unit is further configured to determine a position of a region in the surface of the substrate-under-test, in which region at least one of the flatness, cleanliness and hydrophilicity/hydrophobicity on the surface of substrate is beyond a predetermined value based on the image information.

* * * * *